United States Patent [19]

Neumann

[11] 4,395,423
[45] Jul. 26, 1983

[54] POLYCYCLIC CYANOKETONES

[75] Inventor: Helmut C. Neumann, East Greenbush, N.Y.

[73] Assignee: Sterling Drug Inc., New York, N.Y.

[21] Appl. No.: 100,983

[22] Filed: Dec. 6, 1979

Related U.S. Application Data

[63] Continuation of Ser. No. 950,254, Oct. 10, 1978, abandoned.

[51] Int. Cl.$^3$ .................. C07C 121/48; A61K 31/275
[52] U.S. Cl. ...................................... 424/304; 260/464
[58] Field of Search ......................... 260/464; 424/304

[56] References Cited

U.S. PATENT DOCUMENTS 3,070,623 12/1967 Gottfried et al. .................. 560/194
3,296,255 1/1967 Clinton et al. ............. 260/239.55 R

OTHER PUBLICATIONS

Tolstikov et al., "Izvestia Akademi Nauk Kazakhskoi SSR, Seriya Khimicheskaya, 17, 71–78, (1967).
Yasue et al., Yakugaku Zasshi, 93, 296–299, (1973).
The Merck Index, 8th Ed., 1968, p. 502.
Tolstikov et al., Jour. of Gen. Chem., U.S.S.R., 34, (1964), p. 3181.
Tolstikov et al., Zhurnal Obshchei Khimii, 34, (1964), pp. 3133–3134.
C. A., 74, (1971), 54022e, Kim et al.
Kim et al., Izv. Akad. Nauk. Kaz. SSR, Ser. Khim., (1970), 20(6), pp. 49–54.
C. A., 94, (1981), 103626d, Neumann.

Primary Examiner—Joseph Paul Brust
Attorney, Agent, or Firm—Thomas L. Johnson; B. Woodrow Wyatt

[57] ABSTRACT (18β and 18α)-2α-Cyano-3,11-dioxo-olean-12-en-29-oic acids and lower-alkyl esters thereof, useful as ulcer preventing and ulcer healing agents, are prepared from 18β- or 18α-glycyrrhetinic acid, the final step being alkaline cleavage of 18β- or 18α-11-oxo-olean-2,12-dieno[2,3-d]isoxazol-29-oic acid or an ester thereof.

2 Claims, No Drawings

POLYCYCLIC CYANOKETONES

This application is a continuation of my prior copending application Ser. No. 950,254, filed Oct. 10, 1978, now abandoned.

BACKGROUND OF THE INVENTION (a) Field of the Invention

This invention relates to cyanoketones derived from glycyrrhetinic acid and to their preparation and use as ulcer preventing and ulcer healing agents.

(b) Description of the Prior Art

Carbenoxolone (3-O-(β-carboxypropionyl)-11-oxo-18β-olean-12-en-29-oic acid; glycyrrhetinic acid hydrogen succinate) is a known anti-inflammatory agent used for gastic ulcer in the form of its disodium salt; Gottfried and Baxendale U.S. Pat. No. 3,070,623, Dec. 25, 1962.

Tolstikov, Goryev and Simov, Izvestiya Akademi Nauk Kazakhskoi SSR, Seriya Khimicheskaya 17, 71–78 (1967) disclose the preparation of an isoxazole derivative of glycyrrhetinic acid having the formula:

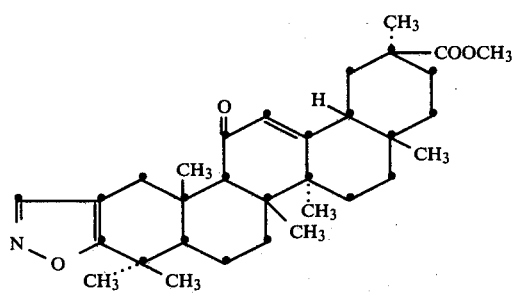

No physiological properties are disclosed for this compound.

Yasue, Sakakibara and Kaiya, Yakugaku Zasshi 93, 296–299 (1973), disclose the preparation of a cyanoketone derived from oleanolic acid, said cyanoketone having the formula:

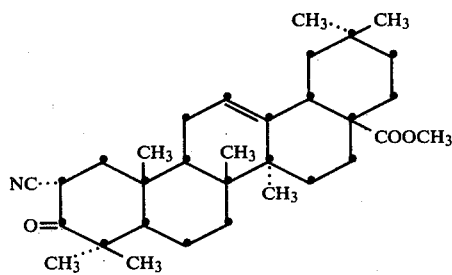

No physiological properties are disclosed for this compound.

The cleavage of isoxazoles to cyanoketones by treatment under alkaline conditions is known in the steroid series; Clinton and Manson U.S. Pat. No. 3,296,255, Jan. 3, 1967.

SUMMARY OF THE INVENTION

In a composition of matter aspect, the invention relates to compounds of the formula:

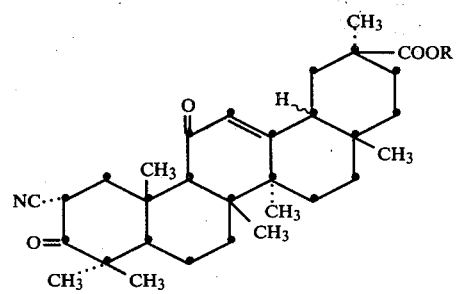

wherein R is hydrogen or lower-alkyl. Also included are 3-lower-alkanoyl enol esters thereof.

Pharmacological evaluation of the compounds of formula I has shown that they are useful in the prevention and/or healing of gastric or intestinal ulcers in mammals.

In a process aspect, the invention relates to a process for preparing a compound of Formula I which comprises reacting a compound of the formula:

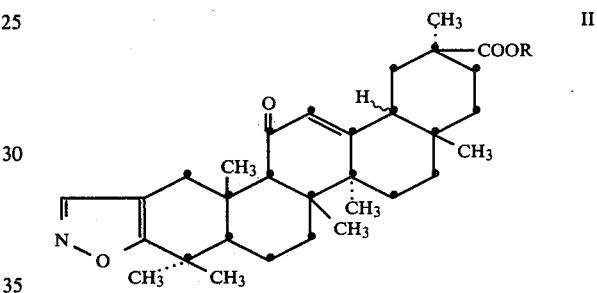

with a strong base until the isoxazole ring has been cleaved, and acidifying the resulting salt of a compound of Formula I.

In a further composition of matter aspect, the invention relates to a composition for the prevention and/or healing of gastric or intestinal ulcers in a mammal which comprises a therapeutically effective amount of a compound of Formula I incorporated in a pharmaceutical carrier suitable for oral administration.

In a further process aspect, the invention relates to a method for the prevention and/or healing of gastric or intestinal ulcers in a mammal which comprises administering orally to said mammal a therapeutically effective amount of a compound of Formula I.

DETAILED DESCRIPTION INCLUSIVE OR PREFERRED EMBODIMENTS

The compounds of Formula I are readily prepared from the commercially available glycyrrhetinic acid or its 18α-isomer. The first step is an oxidation with chromic oxide to yield (18β or 18α)-3,11-dioxo-olean-12-en-29-oic acid. The latter is then treated with ethyl formate in the presence of sodium methoxide in pyridine solution to afford (18β or 18α)-2-hydroxymethylene-3,11-dioxo-olean-12-en-29-oic acid. The hydroxymethylene derivative is reacted with hydroxylamine to produce (18β or 18α)-11-oxo-olean-2,12-dieno[2,3-d]isoxazol-29-oic acid of Formula II. The latter, when treated with a strong base such as an alkali metal hydroxide or alkoxide, undergoes cleavage of the isoxazole ring to form an alkali metal salt of (18β or 18α)-2α-cyano-3,11-dioxoolean-12-en-29-oic acid of Formula I which is readily acidified to form the free acid.

Isomerization of the 18β compounds to the 18α compounds can be effected by treatment with a strong acid at any point in the reaction sequence.

The compounds of Formula I where R is lower-alkyl can be prepared from the compounds where R is hydrogen by conventional esterification reactions, carried out at any point in the reaction sequence. Fischer esterification with a lower-alkanol in the presence of hydrogen chloride will also isomerize the 18β-isomer to the 18α-isomer. The 18β-isomer can conveniently be esterified without isomerization by esterification of the free acid with a 1-lower-alkyl-3-p-tolyltriazene or a diazo-lower-alkane; or by carrying out the reaction sequence described above starting with a known lower-alkyl ester of 18β-glycyrrhetinic acid. The lower-alkyl group R preferably has from one to three carbon atoms.

The lower 3-lower-alkanoyl enol esters of compounds of Formula I can be prepared by heating the latter with a lower-alkanoic acid anhydride in pyridine solution. The lower-alkanoyl group preferably has from two to four carbon atoms, thus being, for example, acetyl, propionyl or butyryl.

The compounds of Formula I are acidic in nature and form alkali metal salts when treated with strong bases such as alkali metal hydroxides or alkoxides. Even the compounds of Formula I where R is lower-alkyl are acidic because of the active hydrogen in the 2-position. Thus, in the cleavage of the isoxazole of Formula II a salt of the 2-cyano-3-oxo compound is initially produced, and said salt is converted to the free 2-cyano-3-oxo steroid by acidification.

The structures of the compounds of the invention were established by the mode of preparation, elementary analysis, chromatographic procedures and infrared and nuclear magnetic resonance spectral determinations.

Pharmacological evaluation of the compounds of Formula I has shown that they are inhibitors of prostaglandin dehydrogenase, which is indicative of their usefulness in the prevention and healing of gastric and intestinal ulcers. This was confirmed by studies which demonstrated that oral administration of the compounds of Formula I to rats and mice caused significant reduction in the incidence of intestinal and gastric ulcers induced by medication with indomethacin.

The compounds of the invention can be prepared for use by dissolving or suspending them in aqueous medium, if necessary with the aid of emulsifying or suspending agents; or by incorporating them in tablet or capsule form with conventional excipients.

The following examples will further illustrate the invention without the latter being limited thereby.

EXAMPLE 1

(a) (5α,18β,30β)-3,11-Dioxo-olean-12-en-29-oic acid.

A mixture of 10 g. of 18β-glycyrrhetinic acid, 3.5 g. of chromic oxide, 50 ml. of acetic acid, 50 ml. of chloroform and 5 ml. of water was kept at room temperature for three hours. The reaction mixture was added to water, ethanol was then added, and the chloroform layer was separated, washed with water, dried and concentrated in vacuo. The residue was recrystallized from a chloroform-ethanol mixture to give 7.75 g. of (5α,18β,30β)-3,11-dioxo-olean-12-en-29-oic acid, m.p. 300°-305° C.(uncorr.).

(b) (5α,18β,30β)-2-Hydroxymethylene-3,11-dioxo-olean-12-en-29-oic acid.

To a solution of 6.96 g. of (5α,18β,30β)-3,11-dioxo-olean-12-en-29-oic acid in 100 ml. of pyridine was added 2.5 ml. of ethyl formate, followed by 1.9 g. of sodium methoxide. The mixture was stirred under nitrogen for seven hours at room temperature and then added to water. The mixture was concentrated in vacuo to a small volume, and 400 ml. of water added, followed by phosphoric acid until the mixture was acidic. The precipitated product was collected, dried, dissolved in tetrahydrofuran, and the solution filtered and concentrated to dryness. The residue was recrystallized from ethyl acetate and from benzene-acetone to give (5α,18β,30β)-2-hydroxymethylene-3,11-dioxo-olean-12-en-29-oic acid, pale yellow prisms, m.p. 299.0°-300° C.(dec.)(corr.), $[\alpha]_D^{25} = +240.0°$ (1% in chloroform); ultraviolet maxima at 251 and 296 mμ ($\epsilon = 13,600$ and 8100); infrared absorption at 2.95, 3.11, 5.78, 6.11 and 6.29μ.

(c) (5α,18β,30β)-11-Oxo-olean-2,12-dieno[2,3-d]isoxazol-29-oic acid [II; R=H, 18β-isomer].

A mixture of 8.25 g. of (5α,18β,30β)-2-hydroxymethylene-3,11-dioxo-olean-12-en-29-oic acid, 1.13 g. of hydroxylamine hydrochloride, 50 ml. of acetic acid and 0.68 g. of sodium acetate was refluxed for thirty minutes. The reaction mixture was diluted with water, and the solid product was collected, washed with water, dried and recrystallized first from ethyl acetate and then from an ethanol-chloroform mixture, to give (5α,18β,30β)-11-oxo-olean-2,12-dieno[2,3-d]isoxazol-29-oic acid, m.p. above 300° C., $[\alpha]_D^{25} = +204.1°$ (1% in chloroform); ultraviolet maximum at 245 mμ ($\epsilon = 13,300$); infrared absorption at 3.11, 3.40, 5.78 and 6.11μ.

(d) (2α,5α,18β,30β)-2-Cyano-3,11-dioxo-olean-12-en-29-oic acid [I; R=H, 18β-isomer].

A mixture of 2.25 g. of (5α,18β,30β)-11-oxo-olean-2,12-dieno[2,3-d]isoxazol-29-oic acid and 0.54 g. of sodium methoxide in 50 ml. of tetrahydrofuran was stirred for two hours at room temperature. Aqueous bicarbonate solution was added to insure the alkalinity of the mixture, and the mixture was concentrated in vacuo. The residue was dissolved in water and the solution acidified with dilute sulfuric acid. The precipitated product was collected, dissolved in tetrahydrofuran, and the solution filtered and concentrated in vacuo. The residue was extracted with an ether-ethyl acetate mixture, and the extracts dried and concentrated. The residue was recrystallized from a tetrahydrofuran-ethyl acetate mixture to give (2α,5α,18β,30β)-2-cyano-3,11-dioxo-olean-12-en-29-oic acid, cream-colored granules, m.p. above 300° C., $[\alpha]_D^{25} = +208.0°$ (1% in chloroform); ultraviolet maximum at 245 μm ($\epsilon = 15,000$); infra-red absorption at 3.11, 3.40-3.45, 4.56, 5.78, 6.11, 6.74 and 6.83μ.

(2α,5α,18β,30β)-2-Cyano-3,11-dioxo-olean-12-en-29-oic acid when tested as an inhibitor of indomethacin-induced ulcers in rats and mice was found to lower the incidence of intestinal ulcers in rats and stomach ulcers in mice from 63% to 0% and from 98% to 53%, respectively.

EXAMPLE 2

(2α,5α,18β,30β)-2-Cyano-3,11-dioxo-olean-12-en-29-oic acid [I; R=H, 18β-isomer].

Sodium methoxide powder (54 g.) was added to a solution of 137.0 g. of (5α,18β,30β)-11-oxo-olean-2,12-dieno-[2,3-d]isoxazol-29-oic acid (Example 1, part c) in 1500 ml. of anhydrous tetrahydrofuran at 10° C. The mixture was stirred under nitrogen for three hours while allowing the mixture to warm to room temperature. The solvent was removed by evaporation in vacuo, 600 ml of water was added to the residue and stripping of volatiles continued to remove residual tetrahydrofuran. The resulting gummy solid was stirred with 1 liter of water and collected by filtration. The product was then dissolved by heating in 350 ml. of glacial acetic acid and 300 ml. of ethanol, decolorized with activated carbon, filtered while hot, seeded, left at room temperature overnight and chilled to 5° C. The solid product which had formed was collected by filtration, washed with hexane and dried in a vacuum oven to give 116.5 g. of (2α,5α,18β,30β)-2-cyano-3,11-dioxo-olean-12-en-29-oic acid, m.p. 309°-310.5° C. This product contained a trace of acetic acid which was removed by further heating under high vaccum at 85° C.

EXAMPLE 3

(5α,18β,30β)-3-Acetoxy-2-cyano-1-oxo-oleana-2,12-dien-29-oic acid [I; R=H, enol acetate].

A mixture of 20 g. of (2α,5α,18β,30β)-2-cyano-3,11-dioxo-olean-12-en-29-oic acid, 20 ml. of acetic anhydride and 40 ml. of pyridine was heated on a steam bath for three hours and then kept at room temperature overnight. Most of the pyridine and excess acetic anhydride were removed by evaporation at reduced pressure. The residue was stirred with ether and methylene dichloride until a colorless solid formed. Some water was added and the solid was collected by filtration and rinsed with ether. The product (19.75 g.) was combined with 4.8 g. obtained from another 5 g. run and recrystallized from an ethylene dichloride-acetic acid mixture to give 17.57 g. of (5α,18β,30β)-3-acetoxy-2-cyano-1-oxo-oleana-2,12-dien-29-oic acid, m.p. 294°-297° C.(decompn.), $[\alpha]_D = +212.9°$ (1% in chloroform).

EXAMPLE 4

(a) Isomerization of 18β-glycyrrhetinic acid

A mixture of 50 g. of 18β-glycyrrhetinic acid and 100 ml. of concentrated hydrochloric acid in 500 ml. of dioxane was heated and stirred on a steam bath for two hours. Water was then added, and the crystalline product which had formed was collected and dried in a vacuum oven at 80° C. to give 48.6 g. of 18α-glycyrrhetinic acid [(3β,5α,18α,30β)-3-hydroxy-11-oxo-olean-12-en-29-oic acid], m.p. 317°-325° C.

(b) (5α,18α,30β)-3,11-Dioxo-olean-12-en-29-oic acid

Chromic oxide (20 g.) was added in portions to a mixture of 49.6 g. of 18α-glycyrrhetinic acid, 300 ml. of methylene dichloride, 400 ml. of acetic acid, 200 ml. of pyridine and 60 ml. of water, cooled to 0° C. The mixture was stirred at room temperature for about 16 hours and then 8 g. of additional chromic oxide was added. The mixture was stirred for five hours longer and the solvent partially removed in a rotary evaporator. The residue was dissolved in 200 ml. of methylene dichloride and extracted with saturated sodium bisulfite solution. The aqueous and organic layers were separated and the organic layer extracted with dilute sodium hydroxide. The solid sodium salt which had formed was collected and washed with methylene dichloride, a few times with boiling ethanol and finally with hot water. A suspension of the sodium salt in water was acidified with hydrochloric acid and extracted with methylene dichloride. The solution was dried over anhydrous magnesium sulfate and concentrated. The residue was crystallized from methanol to give 22.86 g. of (5α,18α,30β)-3,11-dioxo-olean-12-en-29-oic acid in several crops ranging in m.p. from 310° C. to 332° C.

(c) (5α,18α,30β)-2-Hydroxymethylene-3,11-dioxo-olean-12-en-29-oic acid

A mixture of 23.0 g. of (5α,18α,30β)-3,11-dioxo-olean-12-en-29-oic acid, 400 ml. of pyridine and 100 ml. of benzene was stirred and heated in a distillation apparatus until 50-100 ml. of distillate was removed. The mixture was cooled to room temperature, flushed with nitrogen, and 7.2 g. of sodium hydride (dispersion in oil) was added followed by 1 ml. of dry methanol. Methyl formate (22 ml.) was then added dropwise. Reaction was initiated by warming and the mixture was stirred overnight. Additional amounts of sodium hydride (5 g.) and methyl formate (20 g.) were added every few hours on the second day. On the third day, most of the solvent was removed in a rotary evaporator, and the residue was dissolved in water and extracted with ether. The aqueous layer was acidified and extracted with ethyl acetate. The latter solution was dried over anhydrous magnesium sulfate and concentrated to give 15.14 g. of (5α,18α,30β)-2-hydroxy-methylene-3,11-dioxo-olean-12-en-29-oic acid, m.p. 319°-321° C. (decompn.); second crop 6.58 g., m.p. 310°-315° C. (decompn.).

(d) (5α,18α,30β)-11-Oxo-olean-2,12-dieno[2,3-d]isoxazol-29-oic acid [II; R=H, 18α-isomer].

A mixture of 15.14 g. of (5α,18α,30β)-2-hydroxymethylene-3,11-dioxo-olean-12-en-29-oic acid in 300 ml. of ethanol and 100 ml. of tetrahydrofuran was heated at the boiling point until solution was complete. A solution of 2.44 g. of hydroxylamine hydrochloride and 1.3 g. of sodium acetate in 10 ml. of water was then added, and the mixture stirred at reflux for one hour. The reaction mixture was cooled and the solid product collected by filtration. The latter was leached with 300 ml. of isopropyl alcohol, cooled and filtered to give 11.17 g. of (5α,18α,30β)-11-oxo-olean-2,12-dieno[2,3-d]isoxazol-29-oic acid, m.p. 325°-328° C. (decompn.).

(e) (2α,5α,18α,30β)-2-Cyano-3,11-dioxo-olean-12-en-29-oic acid [I; R=H, 18α-isomer].

Sodium methoxide (5.4 g.) was added to a solution of 9.8 g. of (5α,18α,30β)-11-oxo-olean-2,12-dieno[2,3-d]isoxazol-29-oic acid in 200 ml. of tetrahydrofuran and 50 ml. of methanol. The reaction mixture was stirred at room temperature and monitored by thin layer chromatography until reaction was complete in several hours. The mixture was concentrated and the residue dissolved in water and acidified dropwise with 2 N hydrochloric acid. The solid product was collected and recrystallized from a methylene dichloride-ethyl acetate mixture to give (2α,5α,18α,30β)-2-cyano-3,11-dioxo-olean-12-en-29-oic acid in two crops: 5.03 g., m.p. 296°-299° C.

(decompn., vac.); and 3.90 g., m.p. 290°-295° C. (decompn., vac.).

Oral administration of (2α,5α,18α,30β)-2-cyano-3,11-dioxo-olean-12-en-29-oic acid was found to reduce both the incidence and severity of indomethacin-induced gastric and intestinal ulcers in mice. At 100 mg./kg. the severity of gastric ulcers was diminished. At 400 mg./kg. the incidence and severity of both gastric and intestinal ulcers were significantly lowered.

Oral administration of (2α,5α,18α,30β)-2-cyano-3,11-dioxo-olean-12-en-29-oic acid at 200 and 100 mg./kg. completely protected rats against intestinal ulcers induced by indomethacin. Even at 50 and 25 mg./kg., the compound significantly lowered the incidence of ulcers. The $ED_{50}$ was found to be 32 mg./kg.

EXAMPLE 5

(2α,5α,18β,30β)-2-Cyano-3,11-dioxo-olean-12-en-29-oic acid, methyl ester [I; R is $CH_3$, 18β-isomer].

1-Methyl-3-(p-tolyl)triazene (12 g.) was added in portions to a solution of 20 g. of the free acid of Example 1, part (d) in 300 ml. of methylene dichloride, stirred at room temperature. After reaction was complete as indicated by cessation of evolution of nitrogen, the solution was washed with dilute hydrochloric acid and water, dried over anhydrous magnesium sulfate and concentrated. The residue was suspended in ethyl acetate and collected by filtration to give 15.39 g. of product. The latter was combined with the product obtained from another 18 g. run and recrystallized from aqueous dimethylformamide to give 14.0 g. of (2α,5α,18β,30β)-2-cyano-3,11-dioxo-olean-12-en-29-oic acid, methyl ester, m.p. 237°-240° C., containing 0.17 mole of dimethylformamide solvate, $[\alpha]_D = +211.9°$ (1% in chloroform).

EXAMPLE 6

(a) (5α,18β,30β)-11-Oxo-olean-2,12-dieno[2,3-d]isoxazol-29-oic acid, methyl ester [II; R=H, 18β-isomer] was prepared from 49.3 g. of the free acid of Example 1, part (c) with 16.5 g. of 1-methyl-3-p-tolyltriazene according to the procedure of Example 5. There was obtained 48 g. of (5α,18β,30β)-11-oxo-olean-2,12-dieno[2,3-d]isoxazol-29-oic acid, methyl ester, m.p. 277°-279° C. when recrystallized from aqueous dimethylformamide.

(b) The isoxazole methyl ester of part (a) was dissolved in 700 ml. of tetrahydrofuran and 14.9 g. of sodium methoxide was added. The mixture was stirred for 90 minutes and then an additional 2.0 g. of sodium methoxide was added. After stirring the reaction mixture for 30 minutes, it was neutralized with acetic acid and concentrated to dryness. The residue was slurried with hexane and with water to give (2α,5α,18β,30β)-2-cyano-3,11-dioxo-olean-12-en-29-oic acid, methyl ester [I; R is $CH_3$, 18β-isomer], unsolvated, m.p. 213°-217° C. This compound at 200 mg./kg. single oral daily dose for eight days completely prevented the intestinal ulceration caused by a five day 6.0 mg./kg. single oral daily dose of indomethacin.

EXAMPLE 7

(a) (5α,18α,30β)-11-Oxo-olean-2,12-dieno[2,3-d]isoxazol-29-oic acid, methyl ester [II; R=H, 18α-isomer].

(5α,18β,30β)-11-Oxo-olean-2,12-dieno[2,3-d]isoxazol-29-oic acid (Example 1, part c) (10 g.) was added to 200 ml. of methanol saturated with gaseous hydrogen chloride and cooled in an ice-methanol bath. The mixture was stirred vigorously, allowed to come to room temperature and stirred overnight. The solvent was removed and the dry residue triturated with isopropyl alcohol and dissolved in methylene dichloride. The latter solution was washed with sodium bicarbonate solution and concentrated. The residue was slurried with hot ethyl acetate, and the product collected and dried to give 8.8 g. of (5α,18α,30β)-11-oxo-olean-2,12-dieno[2,3-d]isoxazol-29-oic acid, methyl ester. A sample when recrystallized from aqueous dimethylformamide had the m.p. 306°-308° C.

(b) (2α,5α,18α,30β)-2-Cyano-3,11-dioxo-olean-12-en-29-oic acid, methyl ester [I; R is $CH_3$, 18α-isomer] was prepared by treating the isoxazole of part (a) above with sodium methoxide according to the procedure described above in Example 6, part (b), and was obtained as a colorless solid with the m.p. 262°-263.5° C.

I claim:

1. A composition for the prevention and/or healing of gastric or intestinal ulcers in a mammal which comprises a therapeutically effective amount of a compound having the formula

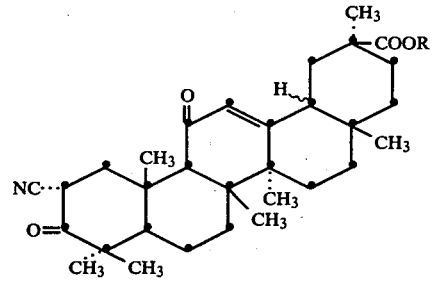

wherein R is hydrogen or lower-alkyl of one to three carbon atoms; a 3-lower-alkanoyl enol ester thereof wherein lower-alkanoyl has from two to four carbon atoms; or an alkali metal salt thereof incorporated in a pharmaceutical carrier suitable for oral administration.

2. A method for the prevention and/or healing of gastric or intestinal ulcers in a mammal which comprises administering orally to said mammal a therapeutically effective amount of a composition according to claim 1.

* * * * *